United States Patent [19]
Ghani

[11] Patent Number: 6,120,811
[45] Date of Patent: *Sep. 19, 2000

[54] MICROGRANULE FOR FOOD/FEED APPLICATIONS AND PROCESS OF MAKING

[75] Inventor: Mahmood M. Ghani, Milpitas, Calif.

[73] Assignee: Genencor International Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/726,231

[22] Filed: Oct. 4, 1996

Related U.S. Application Data

[63] Continuation-in-part of application No. 08/539,896, Oct. 6, 1995, abandoned.

[51] Int. Cl.[7] ............................... A23L 1/052; A23L 1/30
[52] U.S. Cl. .................. 426/61; 426/89; 426/96; 426/103; 426/455; 426/456; 426/463; 426/573; 426/575; 426/576; 426/577; 426/578
[58] Field of Search ................................ 426/61, 573, 89, 426/96, 103, 575, 576, 577, 578, 455, 456, 463

[56] References Cited

U.S. PATENT DOCUMENTS

| | | | |
|---|---|---|---|
| 4,079,125 | 3/1978 | Sipos | 424/32 |
| 4,940,665 | 7/1990 | Iijima et al. | 435/187 |
| 5,254,283 | 10/1993 | Arnold et al. | 435/188 |

*Primary Examiner*—Helen Pratt
*Attorney, Agent, or Firm*—Jeffrey Frazier

[57] ABSTRACT

A microgranular enzyme composition having an average particle size of from about 20 to 400 microns is disclosed. The microgranular composition has low dusting, high blendability and quick dispersion characteristics particularly beneficial to the food and/or feed industries. Also disclosed are methods for making such enzyme-containing microgranules.

7 Claims, No Drawings

MICROGRANULE FOR FOOD/FEED APPLICATIONS AND PROCESS OF MAKING

CROSS-REFERENCE TO RELATED APPLICATIONS

This application is a continuation-in-part of U.S. application Ser. No. 08/539,896 filed Oct. 6, 1995, now abandoned and which is incorporated herein by reference in its entirety.

FIELD OF THE INVENTION

This invention relates to improved enzyme microgranules particularly useful in food and feed applications, as well as agglomeration processes for producing such microgranules.

BACKGROUND OF THE INVENTION

The use of enzymes, especially of microbial origin, has become more common. Enzymes are used in several industries, including but not limited to the starch industry, the dairy industry, the detergent industry and the food or baking industry, as well as the animal feed industry. Many available dry enzyme products are associated with potential industrial hygiene concerns, primarily with regard to the exposure of workers to air-borne enzyme dust, and generally to the dustiness of the available enzyme products. Many granular products useful in the food and feed industries are spray dried. These products tend to be dusty in handling.

Since the introduction of enzymes into the detergent and other industrial segments, many developments have been made regarding the granulation and coating of enzymes to reduce enzyme dust. However, in today's state of ever-increasing environmental concern and heightened awareness of industrial hygiene, there remains a continuing need for low dust enzyme granules. Furthermore, there are additional characteristics desirable in enzyme granules not currently available in known granulation products and particularly for enzyme granule products directed at the food and feed industries. For example, in the food industry a granular enzyme product should incorporate starting materials (such as carriers, binders and coating materials) which are of food grade quality. Furthermore, it is desirable that food enzyme granules be microgranular in size, in other words that they are between 20–400 microns in size, such that the granules blend well with other food ingredients and disperse quickly with even distribution of enzyme when present in an aqueous environment.

Therefore, it is an object of the present invention to provide low dust microgranules having a majority of the particle size within the range of 20–400 microns. These microgranules preferably are dispersible or blendable with food (i.e., baking) ingredients and disintegrate rapidly in an aqueous environment to provide quick availability of the enzyme.

Another object of the present invention is to provide an agglomeration process utilizing fluid bed spraying and drying technology to prepare the low dust microgranules of the present invention.

SUMMARY OF THE INVENTION

According to the present invention there are provided enzyme-containing microgranules comprising:

a) a suitable carrier;
b) an aqueous enzyme source;
c) one or more binder(s) or disintegrant(s); and
d) a water soluble, food grade polymer coating agent;

said microgranule having an average size between 20 to 400 microns, preferably between about 20 to 200 microns.

The enzyme-containing microgranules of the present invention may comprise any enzyme; however, in a preferred embodiment of the present invention, the enzyme is useful in the food and/or baking industry. Thus, useful enzymes include but are not limited to enzymes selected from the group consisting of proteases, amylases, cellulases, xylanases, endoglycosidases and glucose oxidases or mixtures thereof.

This invention also relates to methods for making low dust granules. A method embodiment of the present invention comprises:

a) loading a suitable carrier into a fluid bed granulator;
b) blending an aqueous enzyme source and one or more suitable binder and/or disintegrant agent(s);
c) spraying the blend of enzyme and binder of step b) on the carrier; and
d) spraying the product of step c) with a water soluble, food grade polymer at a rate to form a coating and maintain a particle size from about 20 to 400 microns, preferably 20 to 200 microns;

provided that steps a) and b) can be performed in either order.

DETAILED DESCRIPTION OF THE INVENTION

As used herein, "suitable carrier" means any carrier material which has physical characteristics which are similar to other ingredients used in the food/feed industry. The carrier can be insoluble or soluble in water. Thus, for example, suitable carriers (particularly for the food/baking industry) include but are not limited to soy flour, soy grits, corn flour, ground corn cobs or cellulosic-type material, such as alpha-cellulose powder, regular or spray-dried lactose, maltodextrins, corn syrup solids, etc.

As used herein, "binder" means one or more material(s) which either alone or in combination with sugars (such as sorbitol) act to bind the enzyme to the carrier material, thus forming agglomerates. Binders useful in the present invention include, for example, hydrolyzed starches (such as Miragel or Pure-Gel, commercially available from Staleys, GPC) and gums (such as xanthan gum or locust bean gum). Hydrolyzed starches may be used together with sugars (such as corn syrup solids) as a binder and disintegrant useful in the present invention. Particularly, starch plus corn syrup solids are preferred in the present invention as the combination provides a matrix for fusing the carrier particles together to build the particle size, and the corn syrup solids, which are hydrophilic, help disperse and breakdown the granule in the presence of an aqueous environment (such as the small amount of water used during the dough making process).

As used herein, "water soluble, food grade polymer" means any water soluble, food polymer, including but not limited to high and low viscosity algins and algin blends (such as Keltone™, commercially available from Kelco) and Gellan gum, and blends of such.

Any enzyme or combination of enzymes may be used in the present invention. During a fluidized bed granulation process enzymes are typically sprayed from relatively impure solutions or slurries in which the active enzyme constitutes only a portion of the total dissolved and suspended solids. Other suspended solids present in the fermentation broth include other proteins, peptides, carbohydrates, other organic molecules and salts. Preferred enzymes for the microgranules of the present invention include those enzymes useful in the food (including baking)

and feed industries. Such enzymes include but are not limited to proteases (bacterial, fungal, acid, neutral or alkaline), amylases (alpha or beta), lipases (fungal, bacterial, mammalian), cellulases (whole cellulase or functional components thereof), xylanases and glucose oxidases and mixtures thereof. When the enzyme microgranules of the present invention are to be used in food applications, the enzyme must be of food grade quality. Thus, for example, suitable enzymes include cellulases, lysozymes and proteases available under the Multifect tradename from Genencor International, Inc., Rochester, N.Y. and glucose oxidase available under the OxyGO® tradename from Genencor International, Inc., Rochester, N.Y.

As known to those skilled in the art, other adjunct ingredients may be added to the enzyme microgranules of the present invention. Adjunct ingredients may include: metallic salts, solubilizers, activators, antioxidants, dyes, inhibitors, binders, fragrances, enzyme protecting agents/scavengers such as ammonium sulfate, ammonium citrate, urea, guanidine hydrochloride, guanidine carbonate, guanidine sulfonate, thiourea dioxide, monethyanolamine, diethanolamine, triethanolamine, amino acids such as glycine, sodium glutamate and the like, proteins such as bovine serum albumin, casein and the like, depending on the proposed end use of the microgranule.

A preferred composition of the microgranules of the present invention comprises an active enzyme ingredient useful in the food industry, a soy flour carrier, a modified starch binder which is used in combination with a sugar to bind the enzyme to the soy flour carrier and to act as a disintegrant, and a high viscosity, water soluble, food grade, film-forming, polymer.

Thus, for example, a preferred microgranule of the present invention comprises:

| Ingredient | Amount/100 kg |
|---|---|
| cellulase concentrate (22.5% solids) | 160.0 kg |
| Miragel 463 | 2.0 kg |
| Kelton ™ HV | 200.0 gm |
| corn syrup solids | 8.0 kg |
| soy flour | 53.8 kg |

The skilled artisan will readily recognize that the amount of enzyme will be adjusted according to the activity desired for the finished product. Likewise, the amount of polymer, such as Keltone™, will vary from 0.1 to 0.3% according to the thickness of coating required. The amount of corn syrup used, if any, will vary from 4–15% depending on the volume of enzyme liquid and desired particle size of the finished product, and the amount of carrier (such as soy) will be adjusted based on activity and solids in the enzyme concentrate.

The microgranules of the present invention have an average size of between about $20-400\mu$, preferably $20-200\mu$. The particle size is important because, particularly for the food and baking industries, an enzyme microgranule of this particle size range will blend well with other ingredients in food products (such as dough mixes, etc.)

In a process aspect of the present invention the microgranules are made by agglomeration. This methodology results in lower dust products (as compared to spray dried or freeze dried enzyme products) and more cost effective production. Preferably the microgranules are made in a fluid bed granulator, although other equipment such as oscillating granulators or high shear granulators could be used. A fluid bed granulator is preferred, in part because of the ease of operating the process whereby suitable binders such as sugar and hydrolyzed starch are blended together with a liquid enzyme, which blend is then sprayed onto the carrier. Two objectives are attained during the spraying process: the enzyme is attached to the carrier and the particle is built up to a granular form (within the desired size range). A suitable food grade polymer is then sprayed onto the granulated particles to envelope the enzyme and to hold the agglomerate, or granule, together. This process is economically attractive since the moisture sprayed onto the carrier is "flashed off" as the liquid is sprayed on the carrier, and thus a large amount of aqueous enzyme can be loaded on the carrier.

The three most important parameters for manufacturing the microgranules (falling within the desired particle size of $20-400\mu$) are bed temperature, which should be between about 40–50° C and preferably 42–45° C., fluidization air, which is 300 cubic feet per minute (CFM) at the start and 600 CFM towards the second half of the process, and spray rate, which in a GPCG 300 size granulator is about 1000 ml to 1500 ml/minute, and in equivalent granulators such as a Uniglatt or Vector FL1 is about 15–20 ml/minute or 20–25 ml/minute, respectively.

A general method useful in the present invention is described below and further described by the examples provided herein. The skilled artisan will recognize variations within the specific process parameters, composition components, etc., these variations are within the scope of the present invention.

Generally, a sugar source such as corn syrup solids is dissolved in purified water. This is mixed until the sugar is completely dissolved, after which a modified starch such as Miragel 463 is added to the dissolved sugar solution with mixing, using, for example, an overhead propeller-type mixer. The mixing should continue until the starch is completely hydrated. This solution can be heated, if necessary, to about 40–60° C., preferably 45° C., to increase the hydration process. The enzyme, added in a liquid form either directly from the fermentation broth or in concentrated form, is blended with the binder (starch and/or sugar) solution with mixing. This provides an enzyme/binder blend appropriate for spraying on the carrier.

In the meantime, the fluid bed granulator, similar to a GPCG 300 made by Glatt Air Techniques, should be preheated to an exhaust air temperature of about 60° C. The carrier (for example, soy flour) is loaded into the preheated bowl of the fluid bed granulator and fluidization is started at a low air volume about 300 CFM, sufficient to provide bed movement. This is done at a low air volume because soy flour is very light and is blown into the filters if a higher volume is used. The spray rate is then set at between about 1 liter to 1.5 liter ml/minute, and preferably about 1200 ml/minute, and the enzyme/binder blend is sprayed onto the carrier.

In a separate bowl, a water soluble, food grade polymer (such as Keltone™ HV) is dispersed and hydrated in purified water at room temperature with mixing. The enzyme/binder blend is sprayed until the blend is completely gone and then the spray lines should be flushed with at least 500 ml of purified water. After the lines are flushed, the polymer solution is sprayed at a rate of 1000 to 1200 ml/minute, a rate sufficient to form a coat and maintain the desired small particle size ($20-400\mu$, preferably $20-200\mu$). Excessive spray volume should be avoided so that large aggregates are not formed. The polymer solution should be sprayed until the solution is gone.

The product is dried with 5–10 minutes drying time and passed through a sieve or mesh of about 45 US mesh (350μ size) to remove any aggregates from the finished product.

Typical processing conditions useful in the present invention are described in Table I.

TABLE I

|  | Uniglatt | Vector FL1 | Glatt GPCG 300 (or equivalent) |
|---|---|---|---|
| Air Volume | 40–50 CFM starting | 40 CFM starting | 300–350 CFM starting |
| Inlet Temp | 70–80° C. | 75–80° C. | (set to maintain 42–45° C. exhaust air temp) |
| Exhaust Air and Temp | 42–45° C. | 42–45° C. | 42–45° C. |
| Spray Rate | 15–20 ml/ minute | 20–25 ml/ minute | 1.2–1.4 liters/ minute |
| Nozzle | 1.2 mm single | 1.2 mm single | 2.2 mm single |
| Atomization Air | 20–30 CFM | 20–22 psi | 80 psi |

Procedure for Measuring Disintegration of Granules

Equipment:

1000 ml size beaker and a rotating basket (mesh size approximately 600 microns) attached to a motor.

Procedure:

Place 1000 ml of deionized water in a beaker at room temperature. Weigh out 500 mg of the enzyme granules in the basket and close the basket. Attach the basket rod to a motor. Set the rpm at 40 and lower the basket into the water beaker. Rotate the basket for one minute at 40 rpm and remove from the beaker, all the enzyme granules should disintegrate in the basket.

Preferred dissolution for granules described herein is less than or equal to one minute.

The following examples are representative and not intended to be limiting. One skilled in the art could choose other enzymes, cores, particles, methods and coating agents based on the teachings herein.

EXPERIMENTAL

Example 1

448.9 g of ground corn cob were charged into a preheated Uniglatt fluid bed granulator. 500 ml of liquid cellulase concentrate (5214μ/ml of Multifect® CL, commercially available from Genencor International, Inc.) containing 1 g of Miragel 463 (hydrolyzed starch) as a binder was sprayed onto the ground corn cob at 20 ml/minute so as not to form aggregates. Bed temperature was maintained between 40–45° C. during the spray cycle.

0.1 g xanthan gum was dispersed and hydrated in 200 ml of deionized water. This solution was sprayed onto the enzyme/ground corn cob granulates (which were previously milled to a particle size in the range of below 100 μ) under similar conditions as the previous step. The product was dried to a moisture level of 5–6%.

Example 2

269.5 g of ground corn cob and 200 g of maltodextrin were charged into a preheated Uniglatt fluid bed granulator. 5 g of Miragel 463 and 0.5 g of Keltone™ HV were dispersed in 200 ml of deionized water and hydrated using a homogenizer. This solution was blended with cellulase liquid concentrate (Multifect CL, commercially available from Genencor International, Inc.) and sprayed onto the carrier at 18 ml/minute. Bed temperature was maintained at 42–45° C. during the spray cycle. Product was dried to a moisture level of 5–6%. Particle size of the starting material was controlled by using the starting material in the required particle size range.

Example 3

446 g of soy grits were charged into a preheated Uniglatt fluid bed granulator. 25 g of corn syrup solids and 4 g of starch (Tender-Jel 479, commercially available from Staleys) were dispersed and hydrated in 200 ml of deionized water. This was blended with 100 ml of cellulase enzyme (Multifect CL, commercially available from Genencor International, Inc.). The enzyme and binder solution were sprayed onto the soy grits. Bed temperature during the spray cycle was maintained at 40–42° C. Product was dried to an exhaust temperature of 50–52° C.

Example 4

886 g of soy grits were charged into the preheated bowl of a FL-1 (Vector) fluid bed granulator. Starch binder solution was prepared by mixing 10 g of Tender-Jel in 100 ml of deionized water until fully hydrated. This solution was mixed into 1000 ml of xylanase concentrate (GC140, commercially available from Genencor International, Inc.).

A separate coating solution was prepared by dissolving Keltone™ (commercially available from Kelco) and Maltrin 100 in 200 ml of deionized water. Enzyme/binder solution was sprayed at 20–25 mls/minute onto the soy grits while the fluid bed granulator was kept at a bed temperature of about 38–40° C. The granulated product was coated using the Keltone™/Maltrin coating solution prepared earlier. Final product was dried to a bed temperature of 50–52° C.

Example 5

Soy flour was agglomerated using corn syrup solids base concentrate of 10 g corn syrup solids per 100 g of soy flour. Corn syrup solids were dissolved in water and sprayed at 25 ml/minute onto the soy flour in a fluid bed granulator (Vector Fl-1). This agglomerated soy flour was dried and used as a carrier for manufacturing baking granules using the following procedure: 20 g of Miragel 463 (commercially available from Staleys) (hydrolyzed starch) was dispersed and hydrated in 200 ml of deionized water. This binder solution was blended with 1500 ml of cellulase (Multifect CL from Genencor International, Inc.). 678 g of soy agglomerate prepared as described above were charged in a Vector FL-1 fluid bed granulator with a spray rate of 15 ml/minute. The enzyme/binder solution was sprayed onto the soy agglomerate. 2 g of Keltone™ HV (commercially available from Kelco) (algin) was dispersed and hydrated in 660 ml of deionized water. This algin solution was sprayed onto the granulated product in the fluid bed granulator. Bed temperature was maintained at about 40° C. during the spraying process. Finished product was dried to a bed temperature of 55° C.

Particle size distribution for the granules made in this example were measured, data are provided in Table II. The data show that the majority of particles are between the 20–400 micron range described herein.

TABLE II

Particle Size Distribution for Multifect CSG

| Sieve Size | Weight of Seive* | Weight of Sieve & Product* | Net Wt.* | % Distribution |
|---|---|---|---|---|
| 425µ | 40.2 | 40.5 | 0.3 | 8.3 |
| 250µ | 37.4 | 40.0 | 0.6 | 16.7 |
| 150µ | 35.1 | 36.8 | 1.7 | 47.2 |
| 106µ | 33.9 | 34.2 | 0.3 | 8.3 |
| 90µ | 33.4 | 33.7 | 0.3 | 8.3 |
| 75µ | 33.0 | 33.2 | 0.2 | 5.6 |
| 63µ | 33.5 | 33.7 | 0.2 | 5.6 |
| Pan Bottom | 217.3 | | | |

*grams

Example 6

Product was prepared using the soy agglomerates made using corn syrup solids as the carrier. Binder for enzyme was 3 gm of Kelgum (commercially available from Kelco) in 200 ml of deionized water. Kelgum solution was mixed with barley beta-amylase (commercially available from Neson) and sprayed at 15–16 ml/minute onto soy agglomerates in a fluid bed granulator. 2 g of Keltone™ HV was dispersed and hydrated in 500 ml of deionized water. This algin solution was sprayed at 15 ml/minute onto the granulated enzyme/soy flour at a rate to form a fine coating. Bed temperature of approximately 40° C. was maintained during the granulating and coating process. The finished product was dried to a bed temperature of 52–55° C.

Example 7

A batch of cellulase baking granules was prepared using Miragel 463 starch as the binder. Batch size was 1.0 kg. All the procedures were similar to the batch made as per Example 6.

Example 8

A batch of glucose oxidase was manufactured with soy agglomerates using agglomerated soy flour as the carrier. The granulated product was coated with algin. Batch size was 1.0 kg with 600 ml of liquid enzyme concentrate (OxyGO®, commercially available from Genencor International, Inc.) and 0.2% algin (i.e., 2.0 g per 1.0 kilo batch size).

Example 9

1514.4 g of soy flour was used as a carrier. 160 g of corn syrup solids were dissolved in 1000 ml of deionized water. 40 g of Miragel 463 (starch) was dispersed and hydrated in the above solution and then mixed with the liquid cellulase. Soy flour was charged into a preheated fluid bed granulator (Vector FL-1). Cellulase enzyme/binder solution was sprayed at 22–24 ml/minute onto the soy flour at a rate as not to cause formation of aggregates. Bed temperature was maintained between 40–45° C. during the spray cycle.

4 g of Keltone™ HV was dispersed and hydrated in 1200 ml of deionized water. This solution was spray coated onto the enzyme/soy flour granules.

Example 10

758 g of soy flour and 20 g of Miragel 463 were charged into a preheated Vector FL-1 fluid bed granulator. 120 g of corn syrup solids were dissolved with 200 ml of water which was warmed to 45° C. to aid dissolution. The corn syrup solid solution was blended with 1000 ml of xylanase (GC140, commercially available from Genencor International, Inc.). The xylanase/corn syrup solid blend was sprayed onto the soy flour and Miragel at a spray rate of 25 ml/minute. The fluidization rate was adjusted as necessary as to accommodate the powder bed as it became wet. Bed temperature was maintained between 40–45° C. during the spray cycle.

The product was dried for five minutes. Final product was dried to a bed temperature of 50–52° C. The product was then removed from the oscillator bowl and milled through a size 50 US mesh using an oscillator granulator. 2.0 g of Keltone™ HV (algin) was dissolved in 400 ml deionized water using a propeller-type mixer. The milled product was charged into the preheated Vector FL-1 fluid bed granulator. After flushing the lines with deionized water, the Keltone™ HV solution was sprayed on the milled product at a rate of 20 ml/minute. The final product was dried for 5 minutes. Final product was dried to a bed temperature of 50–52° C.

What is claimed:

1. An enzyme-containing microgranule comprising:
   a) a suitable carrier;
   b) an aqueous enzyme source;
   c) one or more binder(s) or disintegrant(s); and
   d) a water soluble, food grade polymer coating agent;
   said microgranule having an average size between 20 to 400 microns.

2. A microgranule of claim 1 wherein the enzyme is selected from one or more of the group consisting of protease, amylase, lipase, cellulase, xylanase, glucose oxidase and mixtures thereof.

3. A method for making an enzyme-containing microgranule, said method comprising:
   a) loading a suitable carrier into a fluid bed granulator;
   b) blending an aqueous enzyme and one or more suitable binder or disintegrant agent(s);
   c) spraying the blend of step b) on the carrier; and
   d) spraying the product of step c) with a water soluble, food grade polymer at a rate to form a coating and to maintain a particle size from about 20 to 400 microns.

4. A process of claim 3 further comprising preheating the fluid bed granulator.

5. A process of claim 3 further comprising starting fluidization of the carrier in the fluid bed at a low air volume.

6. A process of claim 3 further comprising drying the microgranules at a temperature of about 50° C.

7. A process of claim 3 further comprising passing the microgranule through a sieve of about 350µ size.

* * * * *